United States Patent
Arima

(10) Patent No.: US 9,250,219 B2
(45) Date of Patent: Feb. 2, 2016

(54) COLUMN OVEN FOR LIQUID CHROMATOGRAPH

(71) Applicant: SHIMADZU CORPORATION, Kyoto (JP)

(72) Inventor: Yoshinori Arima, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 337 days.

(21) Appl. No.: 13/788,052

(22) Filed: Mar. 7, 2013

(65) Prior Publication Data

US 2013/0277350 A1    Oct. 24, 2013

(30) Foreign Application Priority Data

Apr. 18, 2012 (JP) .................. 2012-094362

(51) Int. Cl.
*H05B 1/00* (2006.01)
*G01N 30/30* (2006.01)

(52) U.S. Cl.
CPC ........ *G01N 30/30* (2013.01); *G01N 2030/3084* (2013.01)

(58) Field of Classification Search
CPC .................. G01N 30/30; G01N 30/54; G01N 2030/3084; G01N 2030/3061
See application file for complete search history.

(56) References Cited

U.S. PATENT DOCUMENTS

2007/0210065 A1    9/2007    Sohn et al.

FOREIGN PATENT DOCUMENTS

| CN | 201623170 U | 11/2010 |
|----|----|----|
| JP | 58-19259 U | 7/1956 |
| JP | 62-99858 U | 6/1987 |
| JP | 62-143260 U | 9/1987 |
| JP | 2000-111536 A | 4/2000 |
| JP | 20001111536 | * 4/2000 |
| JP | 2004-204810 A | 7/2004 |
| JP | 2011-252719 A | 12/2011 |

OTHER PUBLICATIONS

Chinese Office Action dated Jun. 24, 2014, issued in corresponding Chinese Patent Application No. 201310116249.4 with partial English translation (8 pages).

Office Action dated Apr. 21, 2015, issued in corresponding Japanese application No. 2012-094362, with English translation (6 pages).

* cited by examiner

*Primary Examiner* — Shawntina Fuqua

(74) *Attorney, Agent, or Firm* — Westerman, Hattori, Daniels & Adrian, LLP

(57) ABSTRACT

A column oven for a liquid chromatograph includes a temperature control mechanism possessing a heater, which controls a temperature, and a thermally conductive column holding member in contact with the temperature control mechanism for holding an analytical column of a liquid chromatograph and for transferring heat from the temperature control mechanism to the analytical column. The column holding member includes a space for containing the analytical column. The space is formed to have an opening on one side surface of the column holding member and to have a cross-sectional shape forming a part of an involute curve along a vertical direction with respect to a longitudinal direction of the analytical column held in the column holding member.

4 Claims, 2 Drawing Sheets

COLUMN OVEN FOR LIQUID CHROMATOGRAPH

BACKGROUND OF THE INVENTION

1. Field of the Invention

The present invention relates to a column oven for controlling a temperature of an analytical column of a liquid chromatograph to a predetermined temperature.

2. Description of the Related Art

A liquid chromatograph analytical system is provided with a column oven for controlling, to a predetermined temperature, an analytical column for separating a sample into components. The column oven includes a thermally conductive column holding member for holding the analytical column, and controls the temperature of the analytical column by transferring heat from a heater to the analytical column via the column holding member.

Analytical columns of various outer diameters exist. Therefore, the column holding member of a conventional common column oven has a cross-sectionally V shaped groove which is opened at the top so as to be able to cope with various types of analytical columns, and sandwiches and holds an analytical column in the groove (see JP 2000-111536 A).

The structure as described above of sandwiching and holding an analytical column in a V-shaped groove of a column holding member has an advantage that it can cope with analytical columns of various diameters, but it also has disadvantages that there will be a large gap between the inner side wall of the V-shaped groove and an analytical column and that the area of the opening of the V-shaped groove is large. Due to these disadvantages, desirable heat transfer efficiency is not obtained between the column holding member and an analytical column, and the amount of heat released by the column holding member is increased. If the efficiency of heat transfer from the column holding member to an analytical column is low, there are issues that it takes a long time for the analytical column to reach a target temperature, and also that, since the amount of heat released by the column holding member is great, the temperature distribution of the analytical column becomes uneven.

SUMMARY OF THE INVENTION

An object of the present invention is to improve the heat transfer efficiency between a column holding member and an analytical column in a column oven, and to reduce the amount of heat released by the column holding member.

The present invention is a column oven for a liquid chromatograph, including a temperature control mechanism possessing a heater, which controls a temperature, and a thermally conductive column holding member in contact with the temperature control mechanism for holding an analytical column of a liquid chromatograph and for transferring heat from the temperature control mechanism to the analytical column. The column holding member includes a space for containing the analytical column. The space is formed to have an opening on one side surface of the column holding member and to have a cross-sectional shape forming a part of an involute curve along a vertical direction with respect to a longitudinal direction of the analytical column held in the column holding member.

According to the column oven of the present invention, the column holding member has the space for containing the analytical column, and the space has the opening on one side surface of the column holding member and the cross-sectional shape forming a part of an involute curve along a vertical direction with respect to a longitudinal direction of the analytical column, and thus, the proportion of a gap inside the space inside the column holding member at the time of holding the analytical column can be made smaller compared to a case of sandwiching and holding the analytical column in a V-shaped groove. This enables to improve the heat transfer efficiency between the column holding member and the analytical column. Further, the area of the opening can be made smaller compared to a case of sandwiching and holding the analytical column in a V-shaped groove, and the amount of heat released by the column holding member can be reduced.

DETAILED DESCRIPTION OF THE INVENTION

In a preferred embodiment of the present invention, the cross-sectional shape of a column holding member along a vertical direction with respect to a longitudinal direction of an analytical column is uniform from an upstream end to a downstream end in a flow direction of the analytical column. If the cross-sectional shape of a part of the column holding member is formed to draw an involute curve, the heat transfer efficiency between the column holding member and the analytical column is improved compared with a case where the analytical column is held with being sandwiched in a V-shaped groove, but if the overall cross-sectional shape of the column holding member is uniformly formed to draw an involute curve, the heat transfer efficiency may be further improved, and the temperature of the analytical column may be uniformly controlled.

In a further preferred embodiment of the present invention, the cross-sectional shape of the column holding member along the vertical direction with respect to the longitudinal direction of the analytical column has a recess which is curved to below a bottom end of an opening, and is formed to reach an upper end of the opening while drawing a part of an involute curve. This enables the column holding member to easily hold the analytical column.

Figure 1A:
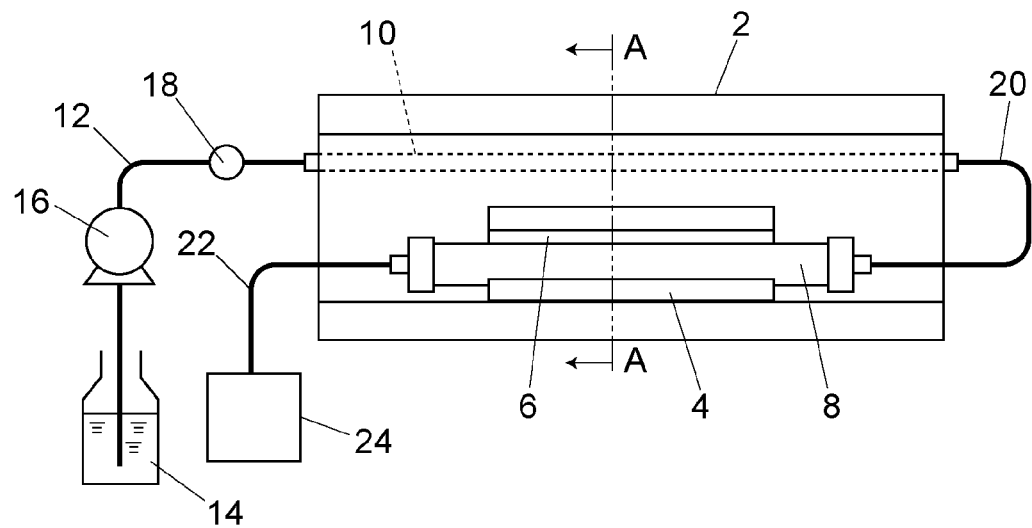
FIG. 1A is a diagram showing a column oven of an embodiment together with a liquid chromatograph, and is a structural diagram of the liquid chromatograph seen from the front side of the column oven.
Figure 1B:
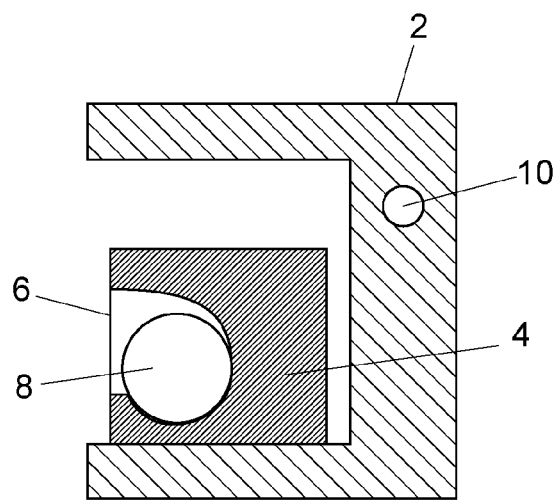
FIG. 1B is a cross-sectional diagram of the column oven along A-A in FIG. 1A.

FIGS. 1A and 1B show a column oven of an embodiment together with a liquid chromatograph.

The column oven includes a temperature control block 2, a column holding member 4, and a preheater tube 10. The temperature control block 2 is heated by a heater not shown, and is controlled to a specific temperature. The preheater tube 10 is buried in the temperature control block 2. The preheater tube 10 is also controlled to a specific temperature by the heat from the temperature control block 2.

The temperature control block 2 is a metal block of high thermal conductivity and is a cross-sectionally U-shaped member having an opening opened on one side surface of the metal block. The column holding member 4 is arranged, inside the opening of the temperature control block 2, for holding an analytical column 8. The column holding member 4 is also a metal member of high thermal conductivity. A space 6 for containing inside and holding the analytical column 8 is provided on one side surface of the column holding member 4. The space 6 of the column holding member 4 is also opened on one side surface, and the opening of the space 6 of the column holding member 4 and the opening of the temperature control block 2 are provided on the same side. The column holding member 4 transfers the heat from the temperature control block 2 to the analytical column 8 held within the space 6. The temperature of the analytical column 8 is thereby controlled to a specific temperature.

One end of a mobile phase passage 12 is connected to one end of the preheater tube 10, and the other end of the preheater tube 10 is connected to one end of the analytical column 8 through a column connection passage 20, and moreover, the other end of the analytical column 8 is connected to a detector 24 through a detection passage 22. A liquid chromatograph is thus structured. The mobile phase passage 12 includes a sample injection part 18 for injecting a sample, and is a passage for suctioning in a mobile phase 14 for analysis from the other end by a delivery pump 16 and for delivering the same.

The sample injected from the sample injection part 18 provided along the mobile phase passage 12 is led to the analytical column 8 via the preheater tube 10 by the mobile phase 14 that is delivered by the delivery pump 16. The mobile phase 14 and the sample are controlled in advance to a specific temperature in the preheater tube 10 and are then led to the analytical column 8. The sample led to the analytical column 8 is separated into components, and each component is detected at the detector 24.

Figure 2A:
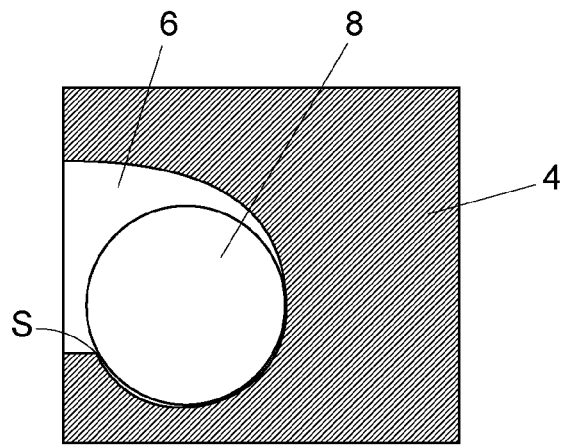
FIG. 2A is a diagram of a column holding member and a column for describing the structure of a column holding member of an embodiment of a column oven.
Figure 2B:
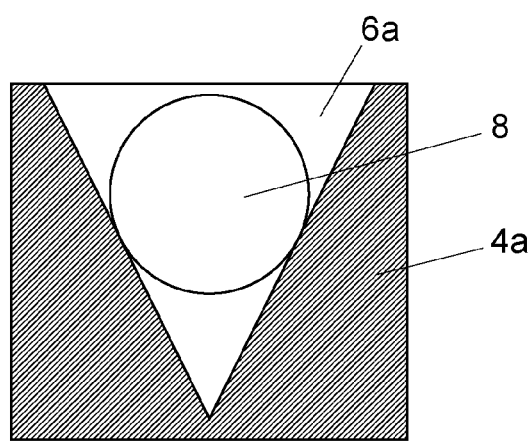
FIG. 2B is a diagram of a column holding member and a column for describing the structure of a column holding member in a conventional column oven.

FIG. 2A shows a cross-sectional diagram of the column holding member 4 of the embodiment cut in a vertical direction with respect to the flow direction. FIG. 2B is a cross-sectional diagram of a conventional column holding member 4a having a V-shaped groove, the column holding member 4a being cut in a vertical direction with respect to the flow direction. The column holding member 4 of the embodiment includes the space 6 for containing the analytical column 8. The space 6 is opened at a side surface of the column holding member 4, and the analytical column 8 is inserted from the opening and is contained. The space 6 has a uniform cross-sectional shape from the upstream end to the downstream end in the flow direction of the analytical column 8.

The cross-sectional shape of a wall inside the space 6 includes a recess which is dented being curved to below the bottom end of the opening at the side surface of the column holding member 4, and the wall is shaped so as to reach the top part of the space 6 while drawing a part of an involute curve from a starting point S of the recess. In the embodiment, the involute curve reaches the upper end part of the opening on the side surface of the column holding member 4. The vertical width of the opening of the space 6 is set so as to allow a column having a maximum outer diameter among columns to be used as the analytical column 8 to be inserted into the space 6.

Since the cross-sectional shape of the space 6 of the column holding member 4 draws a part of the involute curve, the distance from the center of the involute curve to the wall surface on the cross section of the space 6 gradually decreases toward the center of the involute curve, and there will be two contact points with the outer circumferential surface of an analytical column 8 of any outer diameter. By causing the cross-sectional shape of the inside of the space 6 to be such an involute curve, a gap inside the space 6 at the time of holding the analytical column 8 can be made smaller compared to the case of a V-shaped groove 6a as shown in FIG. 2B, and the efficiency of heat transfer to the analytical column 8 may be improved.

An involute curve is a curve expressed by the following formulae. The a is a constant, and the θ is an angle.

$$x = a(\cos\theta + \theta\sin\theta)$$

$$y = a(\sin\theta - \theta\cos\theta)$$

A column which is to be used as the analytical column 8 has, for example, an outer diameter of ¼ to ½ inches, and if a curve within a range of a=1.25 mm and θ=280 to 539°, for example, is adopted as the cross-sectional shape of the inner wall at the back of the space 6, the gap at the time of containing the analytical column 8 will be the smallest.

Here, results of calculating the size (the cross-sectional area) of the gaps formed inside a column holding member when analytical columns whose outer diameters are ¼ inches, ⅜ inches and ½ inches are held in a column holding member whose cross section draws a part of an involute curve (an involute curve) and when they are held in column holding members whose cross section is V-shaped (V-shaped (opening: 45°), V-shaped (opening: 90°)) are shown in Table 1. Additionally, "ratio" in Table 1 represents the size of the gap where the size of the gap of the column holding member whose cross section draws a part of an involute curve is given as 100%.

TABLE 1

| | Outer Diameter of Analytical Column | | | | | |
|---|---|---|---|---|---|---|
| | ¼ Inches | | ⅜ Inches | | ½ Inches | |
| | Cross-Sectional Area of Gap (mm²) | Ratio | Cross-Sectional Area of Gap (mm²) | Ratio | Cross-Sectional Area of Gap (mm²) | Ratio |
| Involute Curve | 154 | 100% | 115 | 100% | 59 | 100% |
| V-shaped (Opening 45°) | 201 | 131% | 162 | 141% | 106 | 180% |
| V-shaped (Opening 90°) | 228 | 148% | 189 | 164% | 133 | 225% |

As shown in Table 1, when a column holding member whose cross-sectional shape draws a part of an involute curve is used, the cross-sectional area of the gap formed inside is the smallest for any of the cases where an analytical column whose outer diameter is ¼ inches, ⅜ inches or ½ inches is used. It is considered that the smaller the proportion of the gap inside the column holding member, the higher the heat transfer efficiency, and thus, by causing the cross-sectional shape of the column holding member to draw a part of an involute curve, the efficiency of heat transfer to an analytical column can be improved.

The invention claimed is:

1. A column oven for a liquid chromatograph, comprising:
a temperature control mechanism possessing a heater, the temperature control mechanism controlling a temperature by the heater; and
a thermally conductive column holding member for holding an analytical column of a liquid chromatograph and for transferring heat from the temperature control mechanism to the analytical column,
the column holding member being arranged in contact with the temperature control mechanism,
the column holding member including a space for containing the analytical column, the space being formed to have an opening on one lateral side surface of the column holding member and to have a cross-sectional shape forming a part of an involute curve along a vertical direction with respect to a longitudinal direction of the analytical column held in the column holding member,
wherein the cross-sectional shape of the column holding member has a recess that is curved to below a lower end of the opening and reaches an upper end of the opening after drawing the part of the involute curve, and
wherein a distance from the center of the involute curve to a wall surface on a cross-section of the space gradually decreases from the upper end of the opening toward the lower end of the opening.

2. The column oven according to claim 1, wherein the cross-sectional shape of the column holding member is uniform from an upstream end to a downstream end in a flow direction of the analytical column.

3. The column oven of claim 1, where the involute curve is a curve expressed by the x and v coordinates in the formulae:

$$x = a(\cos\theta + \theta\sin\theta)$$

$$y = a(\sin\theta - \theta\cos\theta)$$

wherein a is the constant 1.25 mm, and the θ is an angle within the range of 280 to 539°.

4. The column oven of claim 2, where the involute curve is a curve expressed by the x and y coordinates in the formulae:

$$x = a(\cos\theta + \theta\sin\theta)$$

$$y = a(\sin\theta - \theta\cos\theta)$$

wherein a is the constant 1.25 mm, and the θ is an angle within the range of 280 to 539°.

* * * * *